United States Patent [19]

Diaz et al.

[11] Patent Number: 5,369,675
[45] Date of Patent: Nov. 29, 1994

[54] REMOTE LOAD ACTIVATING MECHANISMS

[75] Inventors: Thomas P. Diaz, San Martin; Gary W. Contreras, San Jose; Gerald M. Gordon, Soquel; Veronica L. McCarthy, Fremont; Daniel Weinstein, San Jose, all of Calif.

[73] Assignee: General Electric Company, San Jose, Calif.

[21] Appl. No.: 83,141

[22] Filed: Jun. 25, 1993

[51] Int. Cl.$^5$ .............................................. G21C 17/00
[52] U.S. Cl. ..................................... 376/249; 376/247; 376/245
[58] Field of Search .................... 376/249, 247, 245; 976/DIG. 210; 73/799

[56] References Cited

U.S. PATENT DOCUMENTS

| | | | |
|---|---|---|---|
| 3,909,713 | 9/1975 | Billeter | 324/58.5 C |
| 4,075,884 | 2/1978 | Barker | 73/91 |
| 4,107,980 | 8/1978 | Crane et al. | 73/88 R |
| 4,481,826 | 11/1984 | Ingraffea | 73/799 |
| 4,567,774 | 2/1986 | Manahan et al. | 73/826 |
| 4,592,662 | 6/1986 | Robbins et al. | 374/57 |
| 4,677,855 | 7/1987 | Coffin, Jr. et al. | 73/799 |
| 4,924,708 | 5/1990 | Solomon et al. | 73/799 |
| 5,068,800 | 11/1991 | Brook et al. | 364/507 |
| 5,157,619 | 10/1992 | Palusamy et al. | 364/508 |
| 5,159,563 | 10/1992 | Hiller et al. | 364/507 |

Primary Examiner—Donald P. Walsh
Assistant Examiner—Meena Chelliah
Attorney, Agent, or Firm—J. S. Beulick

[57] ABSTRACT

Electrically controlled load activating mechanisms that can be used inside the containment vessel of a nuclear reactor in conjunction with bellows-loaded DCB crack growth sensors installed inside the reactor pressure vessel or piping of a nuclear reactor. One mechanism is a liquid-filled, double-bellows master/slave arrangement connected by a capillary tube to transmit the loading provided by a linear motion device. Another mechanism uses a heat-resistant gas bottle that can be heated in a furnace to increase the gas pressure to expand the bellows of the DCB sensor. A third mechanism uses a pump or compressor to provide the necessary expansion force. The loading is controlled via electrical connections that do not require special pressure boundary penetrations of the containment vessel.

20 Claims, 5 Drawing Sheets

REMOTE LOAD ACTIVATING MECHANISMS

FIELD OF THE INVENTION

This invention is directed to mechanisms for loading sensors that measure and monitor damage to structural components within aggressive service environments. More particularly, it is directed to mechanisms for activating the load in bellows-loaded double-cantilever beam sensors for measuring crack growth in structural components.

BACKGROUND OF THE INVENTION

When some structural materials are exposed to particular aggressive service environments under steady or cyclic stress, stress corrosion cracking ("SCC") can occur. It is desirable to monitor and assess the extent of damage to structural components due to SCC, for example, in a boiling water reactor ("BWR") which has been operating for a number of years to help predict its lifetime. Crack growth sensors are placed in the core of nuclear reactors as well as in piping flanges outside the core.

Coffin et al. U.S. Pat. No. 4,677,855 discloses a sensor for measuring growth of a preformed crack within a solid exposed to an aggressive environment during application of a load. The crack is defined as possessing a mouth and a tip. The "mouth of the crack" is defined as the point or line of action of load application. The "crack tip" is the leading edge of the crack. The "length" of the crack is defined as the distance from the mouth of the crack to the crack tip. The preformed crack within the solid is of a known length.

The sensor material must be electrically conductive. A current is passed through the solid to establish a voltage drop across the crack. This voltage is measured by at least two pairs of probes, the probes of each pair being positioned on opposite sides of the crack at equal, known distances from the crack mouth.

When a current is caused to flow through the sensor perpendicular to the crack, the potential difference between two points located on opposite sides of the crack will increase as the size of the crack increases. Measurement of the electric potential will provide information as to the instantaneous damage as well as the accumulated damage to the sensor in the form of crack growth.

Figure 1:
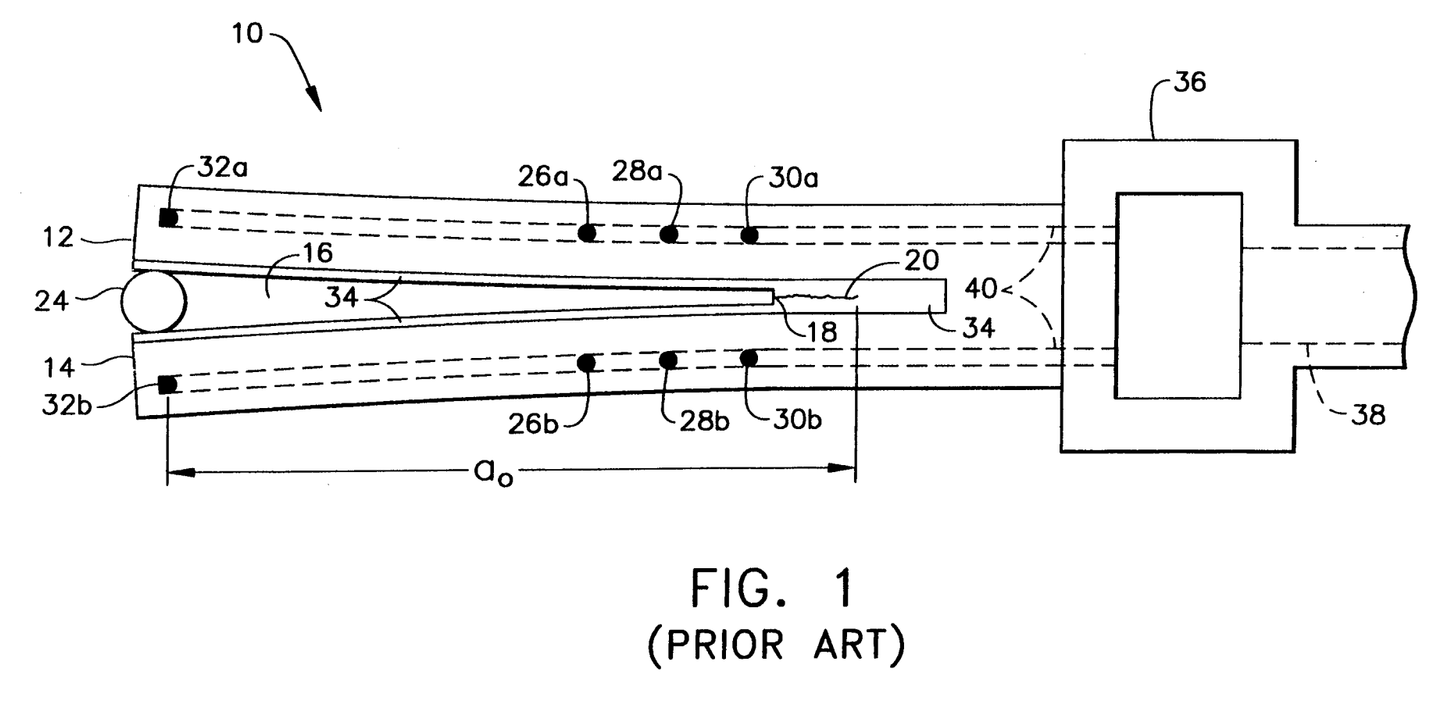
FIG. 1 is a schematic representation of a conventional DCB crack growth sensor.

The configuration of the sensor should permit an applied load of sufficient magnitude to provide a crack tip stress intensity factor that allows the crack to grow at an appropriate rate. A sensor having a double-cantilever beam ("DCB") geometry permits a load of sufficient magnitude to be conveniently applied. As shown in FIG. 1, a sensor 10 with DCB geometry has two parallel arms (beams) 12 and 14 joined at one end and separated at the other. A slot or deep notch 16 separates the arms. The base of this notch is referred to as the notch root 18. The preformed crack 20 is preferably located at the notch root. This configuration permits a number of measurements to be taken at various positions along the beams 12 and 14 since the effective crack length is extended along these beams. The stress intensity is a function of DCB cross section; crack length and applied load. Therefore, the long length of the sensor permits the threshold crack tip stress intensity to be obtained at low load levels.

Side grooves 34 placed within the sensor along the plane of the preformed crack determine the plane in which the crack grows. It is important to keep the fracture surfaces of the crack as planar as possible to avoid multiple cracking and bridging of the crack. Bridging can lead to a short circuit in the current flow and cause errors in the electric potential measurements.

Crack growth is preferably monitored by measuring a potential or voltage across pairs of probes disposed along beams 12 and 14, and using such measured voltages, as well as the initial parameters, to calculate a crack length. At least three pairs of probes $26a/26b$, $28a/28b$ and $30a/30b$ are preferred for accurate measurement of the crack growth.

A pressure boundary 36 which serves as a junction box provides protection for the probe wires from the aggressive environment. Channel 38 provides access to channels (or holes) 40, both of which provide pathways for the conductive leads attached to the probe pairs and to conductive leads which preferably supply a d.c. potential to the sensor. The reversing direct current is supplied at points $32a$ and $32b$ and the effective initial length of the crack is indicated by dimension $a_0$.

For monitoring SCC in aggressive environments, it is conventional practice to apply a fixed displacement to the sensor, thereby causing the preformed crack to grow. A fixed displacement is applied by forcing a wedge 24 into the notch to expand the crack. The wedge must be made of electrically nonconductive material.

When the stress intensity factor is constant at the leading edge of the crack, the resulting rate of crack growth is expected to be constant. Although wedge-loaded DCB crack growth sensors have been successfully used, the stress intensity tends to decrease due to extended crack length and material creep. Thus, actively loaded sensors allowing remote control of the load can compensate for intrinsic load drops due to crack growth, creep and neutron-induced stress relaxation. In addition, load cycling or a change of load level can be performed. This increase in load application flexibility results in a substantial improvement to the sensor design. In essence, elastic energy which is stored in the beams of the DCB specimen is available to cause crack growth when a sufficient load is applied to spread apart the beams. As the crack grows, or as the specimen is heated, the elastic energy in the specimen decreases. In a stiff system, i.e, a sensor that is made of a material with a low compliance, the load drops of rapidly as the crack grows. With the resulting decrease in elastic energy, the rate of crack growth will generally slow down, and if a threshold stress intensity factor is not maintained, the crack growth will arrest completely. Since, without crack growth, no data for predicting crack growth can be generated, this is not a desirable condition. A method of applying a load having a constant stress intensity factor is needed to accommodate for the changing elasticity of the DCB specimen.

SUMMARY OF THE INVENTION

An improved sensor using bellows to control the load has been described in a U.S. patent application entitled "Method and Apparatus for Controlling the Load on Double Cantilever Beam Sensors" and filed concurrently herewith, the disclosure of which is incorporated by reference herein. In the case of in-core sensors, the means of activating the bellows is an area of concern. The tubing connecting the bellows to an activating mechanism outside the drywell is a pressure boundary, which requires a special penetration of the containment vessel. It is therefore desirable to locate the load activating mechanism inside the drywell and control the loading by means which do not require special pressure boundary penetrations of the containment vessel.

The present invention is an electrically controlled load activating mechanism that can be used inside the drywell in conjunction with bellows-loaded DCB sensors. In accordance with a first preferred embodiment, a liquid-filled, double-bellows master/slave arrangement is connected by a capillary tube to transmit the loading provided by a linear motion device. The mechanism of a second preferred embodiment uses a heat-resistant gas bottle and capillary tube that can be heated in a furnace to increase the gas pressure to expand the bellows of the DCB sensor. The mechanism of a third preferred embodiment uses a pump or compressor to provide the necessary expansion force.

DETAILED DESCRIPTION OF THE PREFERRED EMBODIMENTS

Figure 2:
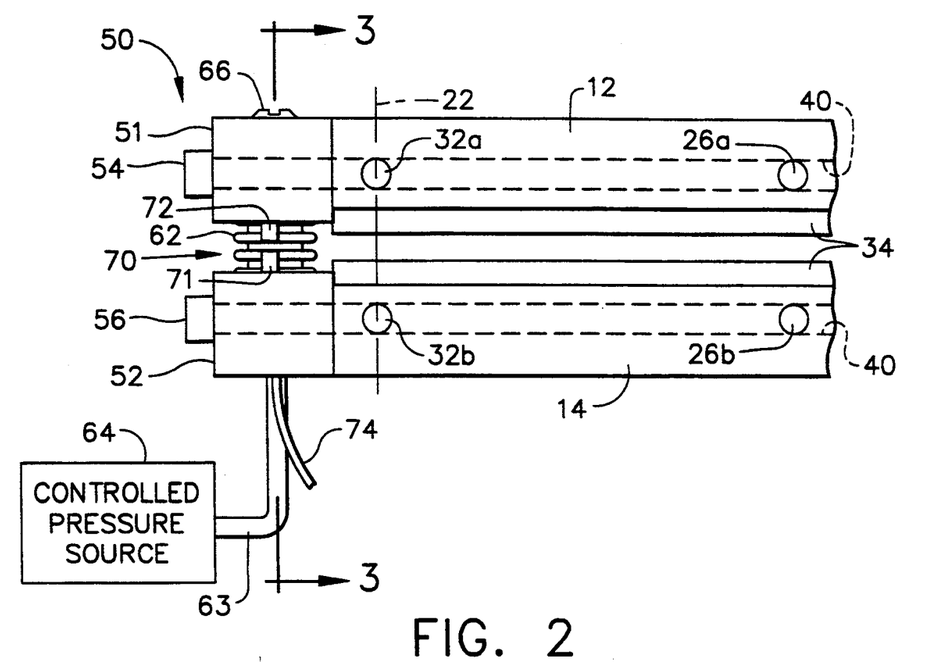
FIG. 2 is a partial elevational view of a DCB crack growth sensor fitted with a bellows loading device and a controlled pressure source.
Figure 3:
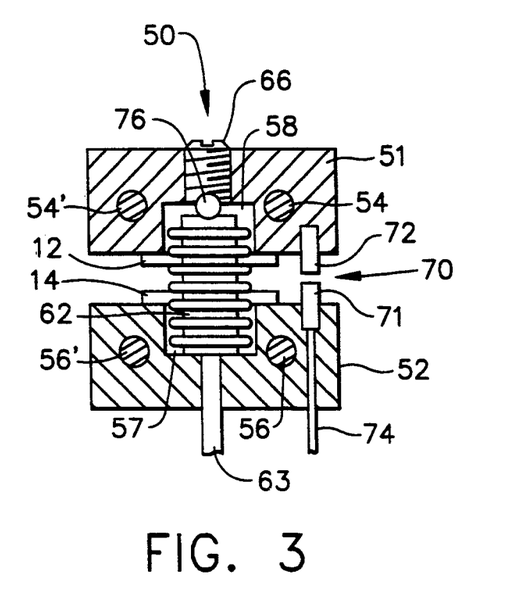
FIG. 3 is a sectional view of the DCB crack growth sensor shown in FIG. 2, taken along section line 3—3.

As disclosed in the aforementioned concurrently filed U.S. patent application entitled "Method and Apparatus for Controlling the Load on Double Cantilever Beam Sensors", a DCB sensor is fitted with a bellows loading device 50 (as shown in FIGS. 2 and 3 herein) which applies a controlled loading. The bellows loading device includes upper and lower mounting blocks 51 and 52 which are secured to the ends of respective beams 12 and 14 by corresponding upper and lower retaining bolts 54, 54' and 56, 56', although other techniques for securing the mounting blocks, such as welding, can be used. Mounting blocks 51 and 52 retain the transfer forces generated by a bellows 62 mounted therebetween. Mounting blocks 51 and 52 are preferably constructed of material having the same coefficient of expansion as the body of the DCB sensor so that changing temperatures will not adversely affect the accuracy of the measured deflections of beams 12 and 14.

As best seen in FIG. 3, one end of bellows 62 is positioned in abutment against the lower, internal surface of a cavity 57 formed within block 52. From cavity 57 the bellows extends to a closed top surface which is located within an upper cavity 58 formed within block 51. Bellows 62 may be constructed of Inconel TM 718 type metal alloy.

Force transfer connection with block 51 from the top of bellows 62 is through a point contact provided by the spherical surface of an intermediate loading ball 76. Ball 76, in turn, provides a self-aligning point contact with block 51 through the lower surface of a set screw 66. The threads of set screw 66 engage the threads of a bore formed within block 51 and communicating with cavity 58. When so configured and attached to the ends of beams 12 and 14, the assembly including mounting blocks 51 and 52 is effective for retaining bellows 62 in an orientation perpendicular to the plane of the preformed crack.

To assure electrical isolation between blocks 51 and 52 in conjunction with this mounting of bellows 62, the surfaces of cavity 57 may be coated with a nonconductive material. Additionally, ball 76 is formed of nonconductive material, such as a ceramic exhibiting low compliance, i.e., little or no deflection under normal loading.

The ball contacting surfaces of bellows 62 and set screw 66 may be constructed with a hemispherical depression in their respective centers such that ball 76 serves as a load centering mechanism to help maintain the load exerted by the bellows normal, i.e., perpendicular, to the surface of the preformed crack. The ball material should be resistant to the aggressive environment in which the DCB sensor is placed.

Porting is provided through the lower mounting block 52 to permit access of the pressurization line to the lower end of bellows 62. A capillary tube 63 extends from the bellows 62, through block 52 and to a controlled pressure source 64 (see FIG. 2), which may supply either pneumatic or hydraulic pressure to bellows 62. However, in certain applications a pneumatic source, for example, an inert gas is preferred to avoid contamination or adverse chemical reactions with the environment in which the DCB sensor is operating in the event of a leak.

Pressures in the range of 2750 psi are sufficient to distend the bellows 62 for loading in-core type DCB sensors. Further, in such nuclear reactor applications, the inlet tube 63 preferably is nearly capillary sized, i.e., about 0.063 inch in outside diameter with a nominal wall thickness of 0.010 inch. Thus, if tube 63 were to rupture within the reactor core, only a very small volume of the pressurizing fluid would be introduced into the reactor. Furthermore, such small tubing will not impose any moment on the DCB sensor. Capillary tube 63 may, for example, be made from Inconel TM 718 material to resist the aggressive environment of a BWR.

Coupled into the mutually inwardly facing surfaces of upper and lower mounting blocks 51 and 52 is a displacement sensor assembly 70, which includes a detector 71 and a target 72. Assembly 70 functions to measure the displacement between beams 12 and 14, and may be any conventional device having an analog voltage output proportional to the distance between the detector and target, such as an eddy current sensor or a Hall effect type sensor.

In the case of an in-core type sensor utilizing bellows-type loading, the total deflection of the bellows is around 0.15±0.05 inch. Therefore, the selected sensor assembly should be capable of producing an output signal having suitable resolution to provide accurate displacement information over this entire range. Such an output signal is conveyed by wiring or lead 74.

In operation, the stress intensity factor required to induce a desired rate of stress related crack growth in a specimen is first determined. The applied stress intensity is a function of the amount of deflection in the beams, given a determinable beam length and a known compliance for the specimen material.

After the beam deflection for a required stress intensity is determined, the DCB sensor is preloaded by mechanically compressing bellows 62 with set screw 66 while monitoring the output of displacement sensor assembly 70. If necessary, the remaining required deflection may be realized by pressurizing the bellows from controlled pressure source 64.

Once the sensor is positioned in situ within a BWR, the rate of stress corrosion cracking is determined using conventional methods. As the length of the crack grows, the amount of load supplied, i.e., the pressure supplied to bellows 62, is adjusted in order to achieve a predetermined stress intensity at the tip of the growing crack. By continually monitoring crack length and making corresponding adjustments in the bellows applied load, the intensity at the crack tip may be held constant, cycled or increased as desired.

Figure 4:
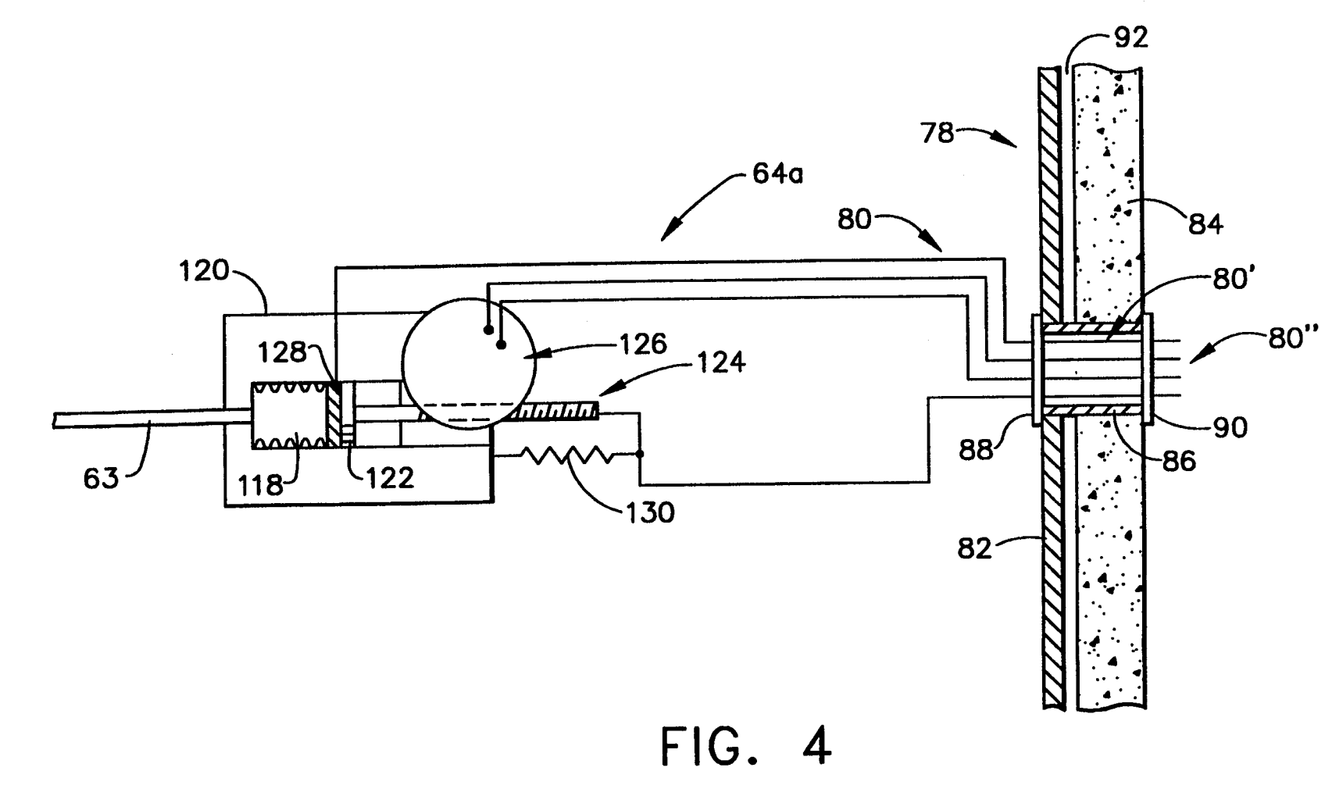
FIGS. 4 through 6 are schematic diagrams showing, respectively, the structure of first, second and third preferred embodiments of the controlled pressure source in accordance with the invention.

A controlled pressure source 64a in accordance with a first preferred embodiment of the invention is shown in FIG. 4. This device consists of a master bellows 118 inside a cylinder 120. The master bellows is compressed by a loading piston 122 connected to a suitable linear motion device 124, such as a threaded shaft. In turn, the linear motion is produced by a suitably geared electric motor 126. The pressure in slave bellows 62 is dependent on the position of piston 122. The master bellows 118 is connected to the DCB slave bellows 62 by means of capillary tube 63. Both the master bellows and the capillary tube are filled with a liquid (such as water) and pressurized to prevent boiling at operating temperatures. Assuming that liquids are incompressible under the pressures needed to load a DCB crack growth sensor, volume reductions of the master bellows 118 produced by the loading piston 122 will cause expansion of the slave bellows 62 (see FIGS. 2 and 3), which in turn will load the DCB crack growth sensor. The pressure in slave bellows 62 is dependent on the position of piston 122. A pressure transducer or load cell 128 situated between the loading piston 122 and the master bellows 118 provides feedback signals for control purposes. Although force (pressure) may be monitored, it is anticipated that displacement will be the main control mode. Displacement control signals can be obtained by attaching a linear variable differential transformer ("LVDT") 130 to the linear motion device 124 and/or using a motor with an encoder.

In operation, geared motor 126 is run until the desired loading is obtained and then the motor is stopped. The mechanical engagement of the gearing will prevent decompression of the master bellows 118. The loading can be cycled by running the motor in reverse and reloading.

The control signals for operating motor 126 and the feedback signals from pressure transducer 128 and LVDT 130 are carried by electrical wires 80, which pass through the drywell 78 to outside the nuclear reactor. The drywell 78 is a steel pressure vessel 82 consisting of a spherical section and a cylindrical section, which is enclosed by reinforced concrete 84 to provide radiation shielding and resistance to buckling and deformation. The concrete is separated from the steel shell 82 by a 2-inch gap 92 to allow for drywell expansion.

The drywell is a pressure boundary. Therefore, penetrations need to be sealed sufficiently to withstand the design pressure. During construction of pre-existing reactors, penetrations are made to allow certain pipes and instrumentation lines to pass through. In addition, penetrations are made for the passage of electrical wires.

Such a pre-existing wire penetration is depicted in FIG. 4. A pipe 86 passes through steel pressure vessel 82 and reinforced concrete wall 84. Electrical wires 80' are passed through pipe 86, which is then sealed with epoxy with the terminals of wires 80' protruding. The protruding terminals are connected to internal and external junction boxes 88 and 90. These electrical wire penetrations are available for use when installing electrical equipment inside the drywell.

When installing bellows-loaded crack growth sensors, the controlled pressure source could be located outside the drywell if a suitable penetration were made in the drywell. However, to make a new penetration would require cutting out portions of the steel section 82 and the reinforced concrete 84, which would be extremely costly and undesirable. Therefore, in accordance with the present invention, the controlled pressure source 64 is placed inside the drywell and the existing electrical wire penetrations are utilized.

As shown in FIG. 4, electrical wires 80 from the controlled pressure source are connected to internal junction box 88 and electrical wires 80'' from the control system (not shown) external to the drywell are connected to external junction box 90. Wires 80 and 80'' are thus electrically coupled via penetration wires 80' to allow control signals, feedback signals, current and power to pass between the controlled pressure source and the control system.

Figure 5:
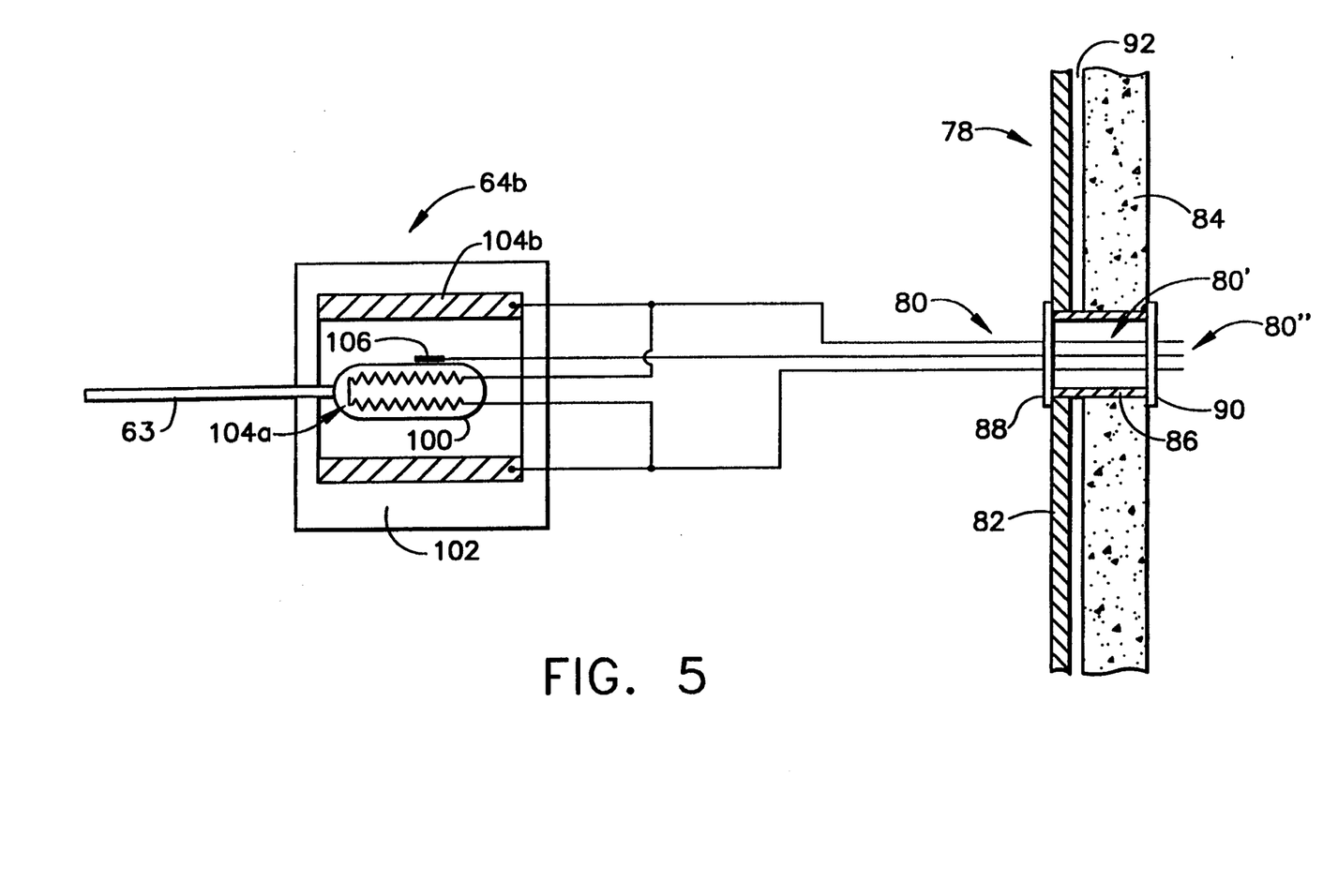

A controlled pressure source 64b in accordance with a second preferred embodiment of the invention is shown in FIG. 5. This device consists of a gas bottle 100 arranged inside a furnace 102 and heated by electrical heating means. The heating means may comprise an internal heater 104a, an external heater 104b or both. In the case of an internal heater, the furnace 102 may be reduced to bottle insulation. The gas bottle is constructed of a heat-resistant alloy to withstand the furnace temperature. The gas bottle is connected by a heat-resistant capillary tube 63 to the DCB bellows 62 (see FIGS. 2 and 3) and filled with a suitable inert gas such as argon. Raising the temperature of the gas bottle causes an increase in pressure which expands the DCB bellows 62, thereby applying the desired load to the DCB sensor. A thermocouple 106 attached to gas bottle 100 provides a feedback signal indicating the temperature of the bottle, which information is used to control the furnace/bottle temperature and the pressure inside DCB bellows 62. Load cycling can be accomplished by cycling the bottle temperature. One advantage of this approach is that no moving parts are needed to pressurize the DCB bellows. The control signals for controlling the heating means and the feedback signals from thermocouple 106 are carried by electrical wires 80, which pass through drywell 78 in the manner previously described with reference to FIG. 4.

Figure 6:
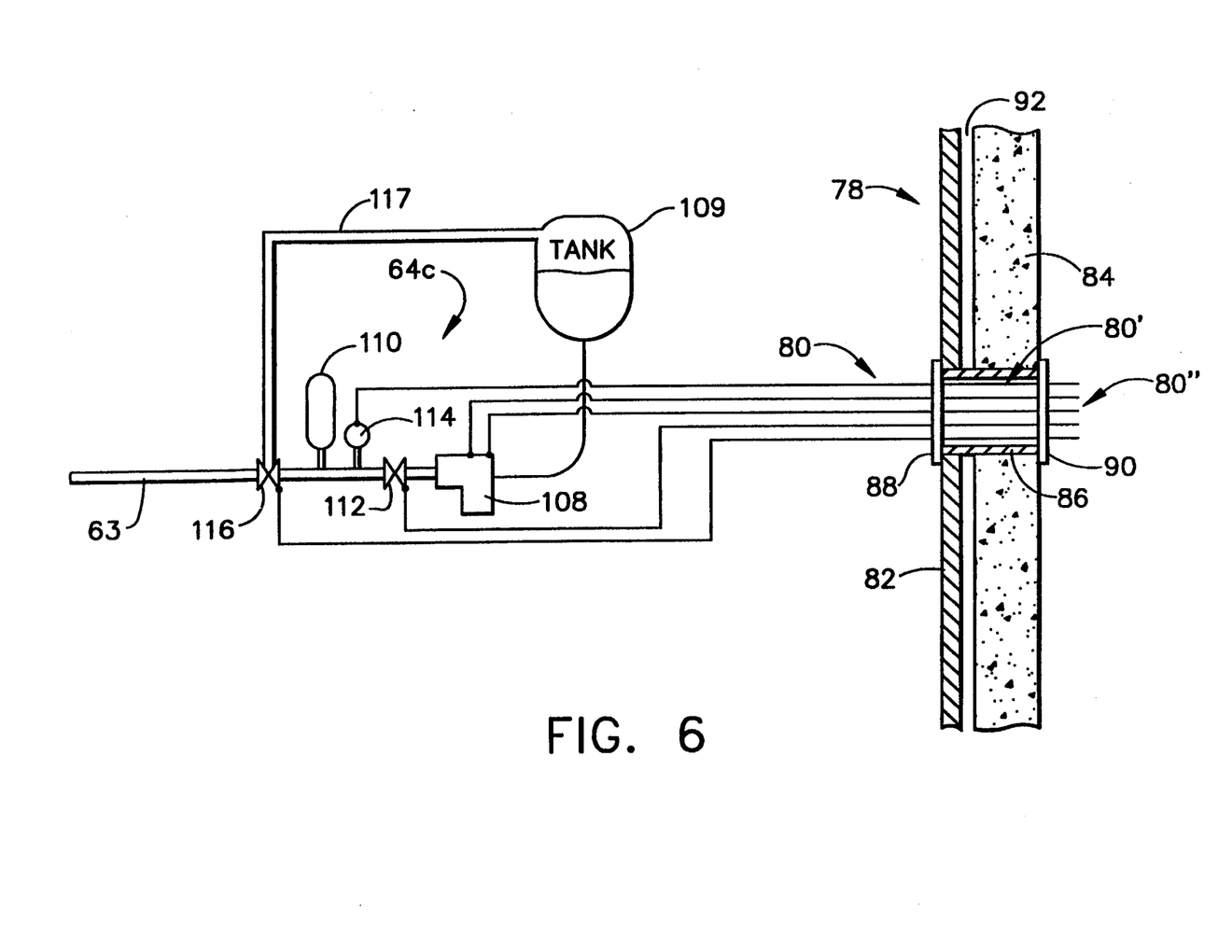

A controlled pressure source 64c in accordance with a third preferred embodiment of the invention is shown in FIG. 6. This device consists of a pump or compressor 108 connected to an accumulator 110 to provide activating pressure to DCB bellows 62 (see FIGS. 2 and 3). The pump/compressor 108 supplies accumulator 110 with fluid from a storage tank 109 located inside the drywell 78. A pressure transducer 114 provides a signal proportional to pressure. When the pressure attains the desired threshold, the pump/compressor is turned off. A remotely activated valve 112 situated between the pump/compressor and the accumulator prevents decompression when the pump/compressor is off. When the pressure falls below the desired threshold, the pump/compressor is restarted.

A pressure relief valve 116 is used to decompress the system if load cycling is desired. The release fluid may be transferred back to tank 109 via relief line 117. The control signals for operating pump/compressor 108 and valves 112 and 116 and the feedback signals from pressure transducer 114 are carried by electrical wires 80, which pass through drywell 78.

The foregoing methods for remote load control were originally conceived for use with in-core/in-flange DCB sensors. However, they can be used for any application where a force is required in some remote location.

Furthermore, other electrically controlled pressure sources suitable for use with bellows-loaded DCB crack growth sensors could be readily designed by a mechanical engineer of ordinary skill. An electrically controlled pressure source can also be used with hollow expandable load-applying means other than bellows. All such variations and modifications are intended to be encompassed by the claims set forth hereinafter.

We claim:

1. An apparatus for pressurizing a hollow expandable device installed inside a reactor pressure vessel or piping of a nuclear reactor, said reactor pressure vessel being surrounded by a drywell having a port for electrical lines, said hollow expandable device having an inlet, comprising:
    an outlet in fluid communication with said inlet of said hollow expandable device;
    means for containing a compressible fluid, said containing means being in fluid communication with said outlet;
    means for changing the pressure of said compressible fluid by a predetermined amount in response to electrical control signals, said pressure changing means being located within the confines of said drywell; and
    a first electrical line passing through said port in said drywell, said first electrical line being connected to said pressure changing means for conducting said electrical control signals thereto from outside the confines of said drywell.

2. The apparatus as defined in claim 1, wherein said containing means comprises a bellows in fluid communication with said outlet, and said pressure changing means comprises a piston connected to a movable end of said bellows and an electric motor coupled to said piston in a manner such that said piston is linearly displaced by operation of said electric motor, the pressure in said hollow expandable device being dependent on the position of said piston.

3. The apparatus as defined in claim 2, wherein said pressure changing means further comprises a threaded shaft connected to said piston, said electric motor comprising gears for engaging the threads on said threaded shaft.

4. The apparatus as defined in claim 3, wherein said electric motor is powered by an electrical power supply carried by a second electrical line which passes through said port in said drywell.

5. The apparatus as defined in claim 3, wherein said electric motor is controlled by said electrical control signals carried by said first electrical line.

6. The apparatus as defined in claim 1, wherein said containing means comprises a gas-filled chamber in fluid communication with said outlet, and said pressure changing means comprises an electric heater for heating the gas in said chamber, the pressure in said hollow expandable device being dependent on the temperature of said gas.

7. The apparatus as defined in claim 6, further comprising means for detecting the temperature of said gas-filled chamber.

8. The apparatus as defined in claim 1, wherein said containing means comprises a storage tank for liquid, and said pressure changing means comprises an electric pump/compressor in fluid communication with said outlet for pumping liquid from said storage tank to said hollow expandable device.

9. The apparatus as defined in claim 8, wherein said pressure changing means further comprises an accumulator in fluid communication with said outlet and with said pump/compressor.

10. The apparatus as defined in claim 9, further comprising valve means for preventing decompression of said hollow expandable device when said electric pump/compressor is off, said valve means being located along the path of fluid communication between said accumulator and said pump/compressor.

11. An apparatus for monitoring crack growth in a reactor pressure vessel or piping of a nuclear reactor, said reactor pressure vessel being surrounded by a drywell having a port for electrical lines, comprising:
    a double-cantilever beam crack growth sensor comprising first and second cantilever beams and a crack formation zone, each of said first and second cantilever beams having one end joined to said crack formation zone;
    a hollow expandable device mechanically coupled at respective ends thereof to the other ends of said first and second cantilever beams, said hollow expandable device being expandable in response to fluid pressure therein, said expanded hollow expandable device exerting a load that urges the other ends of said first and second cantilever beams mutually apart, the magnitude of said load being dependent on the pressure inside said hollow expandable device;
    electrically controllable pressurizing means for supplying fluid having a predetermined pressure to said hollow expandable means, said pressurizing means being located within the confines of said drywell; and
    electrical conducting means for transmitting electrical signals from outside the confines of said drywell to said pressurizing means.

12. The crack growth monitoring apparatus as defined in claim 11, wherein said hollow expandable means comprises a bellows.

13. The crack growth monitoring apparatus as defined in claim 11, wherein said pressurizing means comprises a bellows in fluid communication with said hollow expandable means, a piston connected to a movable end of said second bellows, and an electric motor connected to said electrical conducting means and coupled to said piston in a manner such that said piston is linearly displaced by operation of said electric motor, the pressure in said hollow expandable means being dependent on the position of said piston.

14. The crack growth monitoring apparatus as defined in claim 13, further comprising a threaded shaft connected to said piston, said electric motor comprising gears for engaging the threads on said threaded shaft.

15. The crack growth monitoring apparatus as defined in claim 11, wherein said pressurizing means comprises a gas-filled chamber in fluid communication with said hollow expandable means, an electric heater connected to said electrical conducting means for heating the gas in said chamber and means for detecting the temperature of said gas-filled chamber, the pressure in said hollow expandable means being dependent on the temperature of said gas.

16. The crack growth monitoring apparatus as defined in claim 11, wherein said pressurizing means comprises an electric pump/compressor connected to said electrical conducting means and in fluid communication with said hollow expandable means for pumping fluid therein, and valve means for preventing decompression of said bellows when said electric pump/compressor is off.

17. The crack growth monitoring apparatus as defined in claim 16, further comprising an accumulator in fluid communication with said hollow expandable means and with said pump/compressor, said valve means being located along the path of fluid communication between said accumulator and said pump/compressor.

18. A method for monitoring crack growth in a component of a nuclear reactor using a double-cantilever beam crack growth sensor, said nuclear reactor comprising a reactor pressure vessel surrounded by a drywell, comprising the following steps:
mechanically coupling one end of a hollow expandable device to one end of a first cantilever beam of said crack growth sensor;
mechanically coupling the other end of said hollow expandable device to one end of a second cantilever beam of said crack growth sensor;
installing said coupled hollow expandable device/crack growth sensor inside said reactor pressure vessel or inside piping of said nuclear reactor;
installing an electrically controllable pressure source inside the confines of said drywell in fluid communication with said hollow expandable device;
connecting said hollow expandable device and said electrically controllable pressure source to be in fluid communication; and
establishing an electrical connection between said electrically controllable pressure source and an external source of electrical signals located outside the confines of said drywell.

19. The method as defined in claim 18, further comprising the step of expanding said hollow expandable device using pressurized fluid from said pressure source, said hollow expandable device being expanded by a predetermined amount in dependence on the control signal received by said pressure source from said external source of electrical signals, whereby a predetermined load is applied to said crack growth sensor.

20. The method as defined in claim 18, wherein said electrical connection passes through a sealed port in said drywell.

* * * * *